United States Patent
Dalley et al.

(10) Patent No.: US 11,679,056 B2
(45) Date of Patent: Jun. 20, 2023

(54) ADVANCED GAIT CONTROL SYSTEM AND METHODS ENABLING CONTINUOUS WALKING MOTION OF A POWERED EXOSKELETON DEVICE

(71) Applicant: Ekso Bionics Holdings, Inc., San Rafael, CA (US)

(72) Inventors: Skyler Dalley, Shaker Heights, OH (US); Ryan Farris, Solon, OH (US); Spencer Murray, Aurora, OH (US)

(73) Assignee: Ekso Bionics Holdings, Inc., San Rafael, CA (US)

( * ) Notice: Subject to any disclaimer, the term of this patent is extended or adjusted under 35 U.S.C. 154(b) by 450 days.

(21) Appl. No.: 16/761,928

(22) PCT Filed: Apr. 23, 2018

(86) PCT No.: PCT/US2018/028787
§ 371 (c)(1),
(2) Date: May 6, 2020

(87) PCT Pub. No.: WO2019/156698
PCT Pub. Date: Aug. 15, 2019

(65) Prior Publication Data
US 2020/0323726 A1 Oct. 15, 2020

Related U.S. Application Data

(60) Provisional application No. 62/627,867, filed on Feb. 8, 2018.

(51) Int. Cl.
*A61H 3/00* (2006.01)
*G16H 40/67* (2018.01)
(Continued)

(52) U.S. Cl.
CPC ............ *A61H 3/00* (2013.01); *A61H 1/0262* (2013.01); *B25J 9/0006* (2013.01); *B25J 13/088* (2013.01);
(Continued)

(58) Field of Classification Search
CPC .. A61H 3/00; A61H 1/0262; A61H 2003/007; A61H 2201/5007;
(Continued)

(56) References Cited

U.S. PATENT DOCUMENTS 8,795,207 B2  8/2014  Cavallaro et al.
8,834,169 B2  9/2014  Reinkensmeyer et al.
(Continued)

FOREIGN PATENT DOCUMENTS

| EP | 2 827 809 | 1/2015 |
|---|---|---|
| WO | 2013/142777 | 9/2013 |
| WO | 2017/023864 | 2/2017 |

OTHER PUBLICATIONS

International Search Report and Written Opinion issued by WIPO for corresponding International Patent Application No. PCT/US2018/028787 dated Nov. 18, 2018.

*Primary Examiner* — Amanda K Hulbert
*Assistant Examiner* — Natasha Patel
(74) *Attorney, Agent, or Firm* — Renner, Otto, Boisselle & Sklar, LLP (57) ABSTRACT

A method of controlling an exoskeleton mobility device includes executing a control application with an electronic controller to perform: sensing at least one of an angular position or angular velocity of a stance/trailing leg during a single support dynamic state of a gait cycle; determining whether the angular position satisfies an advanced gait threshold; and when it is determined that the angular position satisfies the advanced gait threshold, the control system (Continued)

employs advanced gait control in which a duration of double support states between single support dynamic states is minimized. For advanced gait control the control system controls such that hip joint component velocities are non-zero during transitions from swing states to stance states, and knee joint component velocities are non-zero during transitions from stance states to swing states of the gait cycle. Each step of the gait cycle thus blends into a next step by way of hip joint component swing-to-stance extension, and/or knee joint component stance-to-swing flexion.

20 Claims, 8 Drawing Sheets (51) Int. Cl.
| | | |
|---|---|---|
| *G16H 40/40* | (2018.01) | |
| *A61H 1/02* | (2006.01) | |
| *B25J 9/00* | (2006.01) | |
| *B25J 13/08* | (2006.01) | |
| *G05B 19/042* | (2006.01) | |

(52) U.S. Cl.
CPC ........... *G05B 19/042* (2013.01); *G16H 40/40* (2018.01); *G16H 40/67* (2018.01); *A61H 2003/007* (2013.01); *A61H 2201/5007* (2013.01); *A61H 2201/5035* (2013.01); *A61H 2201/5069* (2013.01); *A61H 2201/5079* (2013.01); *A61H 2201/5084* (2013.01); *G05B 2219/25257* (2013.01); *G05B 2219/25268* (2013.01)

(58) Field of Classification Search
CPC .... A61H 2201/5035; A61H 2201/5069; A61H 2201/5079; A61H 2201/5084; A61H 2201/165; A61H 2201/5025; A61H 2201/5058; A61H 1/024; A61H 1/0244; B25J 9/0006; B25J 13/088; G05B 19/042; G05B 2219/25257; G05B 2219/25268; G16H 40/40; G16H 40/67; G16H 20/30; G16H 20/40; G16H 40/63; A61F 2002/704; A61F 2/70
See application file for complete search history.

(56) References Cited

U.S. PATENT DOCUMENTS

| | | | |
|---|---|---|---|
| 8,838,263 B2 | 9/2014 | Sivak et al. | |
| 9,072,463 B2 | 7/2015 | Sanders et al. | |
| 10,531,967 B2* | 1/2020 | Lim | A61F 2/72 |
| 2008/0039756 A1 | 2/2008 | Thorsteinsson et al. | |
| 2011/0105966 A1* | 5/2011 | Kazerooni | A61H 1/0255 |
| | | | 601/35 |
| 2012/0172770 A1 | 7/2012 | Almesfer et al. | |
| 2013/0237884 A1* | 9/2013 | Kazerooni | A61H 3/00 |
| | | | 601/34 |
| 2015/0142130 A1 | 5/2015 | Goldfarb et al. | |
| 2017/0027803 A1* | 2/2017 | Agrawal | A61B 5/1122 |
| 2017/0151070 A1 | 6/2017 | Sun et al. | |
| 2018/0008502 A1* | 1/2018 | Asbeck | A61F 5/01 |
| 2018/0360347 A1* | 12/2018 | Lim | A61H 3/00 |
| 2019/0160321 A1* | 5/2019 | Ozsecen | A63B 24/0087 |

* cited by examiner

ADVANCED GAIT CONTROL SYSTEM AND METHODS ENABLING CONTINUOUS WALKING MOTION OF A POWERED EXOSKELETON DEVICE

RELATED APPLICATIONS

This application is a national phase of International Application No. PCT/US2018/028787 filed Apr. 23, 2018, which claims the benefit of U.S. Provisional Application No. 62/627,867 filed Feb. 8, 2018, the contents of which are incorporated herein by reference.

FIELD OF INVENTION

The present invention relates to electronic control systems for a mobility assistance device, such as for example a legged mobility device or "exoskeleton" device, including control systems and methods for advanced gate control that enable a continuous walking motion in such a powered exoskeleton device.

BACKGROUND OF THE INVENTION

There are currently on the order of several hundred thousand spinal cord injured (SCI) individuals in the United States, with roughly 12,000 new injuries sustained each year at an average age of injury of 40.2 years. Of these, approximately 44% (approximately 5300 cases per year) result in paraplegia. One of the most significant impairments resulting from paraplegia is the loss of mobility, particularly given the relatively young age at which such injuries occur. Surveys of users with paraplegia indicate that mobility concerns are among the most prevalent, and that chief among mobility desires is the ability to walk and stand. In addition to impaired mobility, the inability to stand and walk entails severe physiological effects, including muscular atrophy, loss of bone mineral content, frequent skin breakdown problems, increased incidence of urinary tract infection, muscle spasticity, impaired lymphatic and vascular circulation, impaired digestive operation, and reduced respiratory and cardiovascular capacities. In addition to full paraplegia, debilitative health conditions, like strokes and other vascular and neurological impairment, can substantially impair mobility and have the additional secondary physiological effects.

In an effort to restore some degree of legged mobility to individuals with paraplegia or other forms of mobility impairment, several lower limb orthoses have been developed. The simplest form of such devices is passive orthotics with long-leg braces that incorporate a pair of ankle-foot orthoses (AFOs) to provide support at the ankles, which are coupled with leg braces that lock the knee joints in full extension. The hips are typically stabilized by the tension in the ligaments and musculature on the anterior aspect of the pelvis. Since almost all energy for movement is provided by the upper body, these passive orthoses require considerable upper body strength and a high level of physical exertion, and provide very slow walking speeds.

To decrease the high level of exertion associated with passive orthoses, the use of powered orthoses has been under development, which incorporate actuators and drive motors associated with a power supply to assist with locomotion. These powered orthoses have been shown to increase gait speed and decrease compensatory motions, relative to walking without powered assistance.

The use of powered orthoses presents an opportunity for electronic control of the orthoses. Exoskeleton devices to date, however, have lacked comprehensive control systems that also are user-friendly to maximize the effectiveness and comfort for a legged mobility exoskeleton device. Examples of powered orthoses are known. WO/2010/044087, US 2010/0094188, and U.S. Pat. No. 8,096,965 disclose a powered exoskeleton bracing system/exoskeleton bracing system. These prior art devices, however, have been insufficient for comprehensive and user-friendly control of the exoskeleton device. There have been attempts to provide at least generalized control of an exoskeleton device, including the providing of safety indications. For example, U.S. Pat. No. 8,905,955 B2 discloses a method of controlling an exoskeleton bracing system comprising halting actuation of the motorized joints when a signal that is received from a tilt sensor indicates falling. These methods are described entirely within the context of standing and sitting transitions.

WO/2013/142777 discloses a method of controlling a powered lower extremity orthotic, wherein the leg support includes a thigh segment, shank segment, further comprising estimating an angle of the shank segment with respect to vertical. The device is controlled to take a step when the shank angle exceeds a threshold with respect to gravity, and the system further comprises signaling the user when placing the orthotic into a state corresponding to taking a step, the signal generally being accomplished by an auditory tone, haptic vibration, or visual cue. WO/2013/142777 also discloses a related method of controlling a powered lower extremity orthotic, wherein the leg support includes a thigh segment, shank segment. The method comprises estimating an angle of the shank segment with respect to vertical, and the device takes a step when the shank angle exceeds a threshold with respect to gravity. The method further comprises calculating a center of pressure average trajectory over time, calculating the variation of that location over time, and generating a proficiency score. The method further comprises restricting which exoskeleton states may be reached based on at least a threshold of said amount of variation.

Exoskeleton control for walking conventionally occurs as an ordered set of static and stepping states to construct a gait cycle. States generally alternate between "double support" states which are static states in which both feet are planted on the ground, and "stepping" or "single support" states which are dynamic states in which one foot is on the ground and one leg is swinging, or in other words, one leg is in a stance state and the other leg is in a moving swing state. Example static states includes double support states with left foot forward or right foot forward. Example dynamic states include right stepping and left stepping. Biomechanical motion is then controlled by cycling through these states in succession, (e.g. right step (dynamic), right forward (static), left step (dynamic), left forward (static)), and so on, where joint motion is commanded during dynamic states and where joint motion is typically initiated during static states.

Exemplifying the above, in a first type of control referred to as "standard gait", a decision to step is made during the static double support state based principally on angular position thresholds related particularly to a forward leg in the stance state. Such a position may be associated with a center of pressure, which basically is the user center of gravity projected to the ground. A balance point for the center of pressure between toe-off and heel strike provides velocity end points for swing and stance states of the legs, and the decision whether to step could thereby be based on the center of pressure during the static double support stance states. A delay in going from the double support (static) state and the single support stepping (dynamic) swing state may be provided, and a decision whether to step would be made during the double support static state. While this approach is safe, it is also limiting, as joint motion does not occur during static states while user intent is determined (i.e., while the user is standing in double support), and joint velocities fall to in anticipation of such phases (i.e. at the beginning and end of a step). The result is a bit of a "clunky" or non-smooth stepping action in which a significant period of time, also known as the dwell time, is spent in the double support static state between steps.

In a variation of the standard gait control, average angular velocity of the forward leg may be considered as an additional parameter with angular position. Thigh angle and velocity in particular may be employed to determine whether to trigger a step rather than center of pressure. Like the conventional standard gait, however, the decision whether to step in this variation still is made during the static state when no device joint motion is occurring, still requiring a significant dwell time. Accordingly, although the additional use of angular velocity permits a faster step trigger when there is a higher angular velocity, i.e., when the user is capable of moving faster, the general clunky nature of the gait motion essentially remains due to the significant dwell time spent in the double support static state.

SUMMARY OF THE INVENTION

The present invention is directed to a control system and methods for advanced gait control in a powered exoskeleton device. A control method for a powered lower extremity orthosis exoskeleton device is implemented in which at least one joint is always in motion during the gait cycle. In exemplary embodiments, the joint in motion is characterized by stance-to-swing knee flexion, and/or swing-to-stance hip extension, thereby producing a legged motion that is: (1) continuous in nature, and (2) initiated during the dynamic phases of gait, i.e., single support dynamic stepping states, rather than during the double support static states as is conventional.

The advanced gait control methods of the present disclosure, in contrast to the standard gait control described above, allow for joint motion to be initiated during the previous dynamic state, such that intervening static states are unnecessary and dwell time is substantially reduced or eliminated. For example, the decision to make a left step is determined while taking a right step, as opposed to after a right step has occurred and all joints have come to rest in the double support static state (e.g., while in the static, right foot forward state). As such, any delay in motion that would have otherwise occurred due to the cessation of joint motion becomes unnecessary, and the delay to determine user intent is effectively eliminated. Furthermore, as joint motion need not cease between dynamic states, joint motion can instead occur or continue in anticipation of the next dynamic state. The overall effect of the advanced gait control is to produce a continuous motion that enables higher walking speeds, which depends on reliably determining user intent during dynamic states.

The advanced gait control also may be used in conjunction with conventional standard gait approaches described above, allowing the user to transition from slower, staccato cadences as defined by standard gait control, in which steps are separated by periods of rest with significant dwell time, to the faster, legato cadences define by the advanced gait control in which steps flow more continuously into one another with minimal static state dwell time. These transitions depend on determining how rapidly subsequent steps occur.

An aspect of the invention, therefore, is a control method for a mobility assistance device employing advanced gait control. In exemplary embodiments, the control method employs the following steps: providing said mobility device including a control system for controlling operation of the mobility device components to selectively configure and modulate hip and knee joint components to perform a gait cycle; providing within said mobility device a control application to be executed by the control system to control the gait cycle; and providing within said mobility device a plurality of sensors to detect a state of the hip and knee joint components to determine an angular position of the right leg and left leg during the gait cycle. The control system executes the control application to perform the steps of: sensing at least one of an angular position or an angular velocity of a stance/trailing leg during a single support dynamic state of the gait cycle; determining whether the angular position or angular velocity satisfies an advanced gait threshold; and when it is determined that the angular position or angular velocity satisfies the advanced gait threshold, the control system employs advanced gait control of the hip and knee joint components by which a duration of double support states between single support dynamic states is minimized.

For advanced gait control the control system further controls the hip joint components to utilize advanced gait joint trajectories in which hip joint component velocities are non-zero for the hip joint components during transitions from swing states to stance states of the gait cycle, and in which knee joint component velocities are non-zero for the knee joint components during transitions from stance states to swing states of the gait cycle. In this manner, the control system controls the knee and hip joint components such that each step of the gait cycle blends into a next step by way of hip joint component swing-to-stance extension and/or knee joint component stance-to-swing flexion, and at least one joint component is always moving during the gait cycle. When it is determined that the angular position and angular velocity do not satisfy the advanced gait threshold, the control system employs standard gait control in which double support states are maintained between single support dynamic states, and a decision whether to step is made by sensing an angular position of the forward leg during the double support state.

These and further features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended hereto. Features that are described and/or illustrated with respect to one embodiment may be used in the same way or in a similar way in one or more other embodiments and/or in combination with or instead of the features of the other embodiments.

DETAILED DESCRIPTION

Embodiments of the present invention will now be described with reference to the drawings, wherein like reference numerals are used to refer to like elements throughout. It will be understood that the figures are not necessarily to scale.

For context, FIGS. 1-6 depict various views of an exemplary exoskeleton device that may be used in connection with the control system and methods of the present invention. A somewhat generalized description of such exoskeleton device is provided here for illustration purposes. A more detailed description of such device may be found in Applicant's International Patent Appl. No. PCT/US2015/023624 filed on Mar. 3, 2015, which is incorporated here in its entirety by reference. It will be appreciated, however, that the described exoskeleton device presents an example usage, and that the control system and methods of the present invention are not limited to any particular configuration of an exoskeleton device. Variations may be made to the exoskeleton device, while the features of the present invention remain applicable. In addition, the principles of this invention may be applied generally to any suitable mobility device. Such mobility devices include, for example, orthotic devices which aid in mobility for persons without use or limited use of a certain body portion, and prosthetic devices, which essentially provide an electro-mechanical replacement of a body part that is not present such as may be used by an amputee or a person congenitally missing a body portion.

Figure 1:
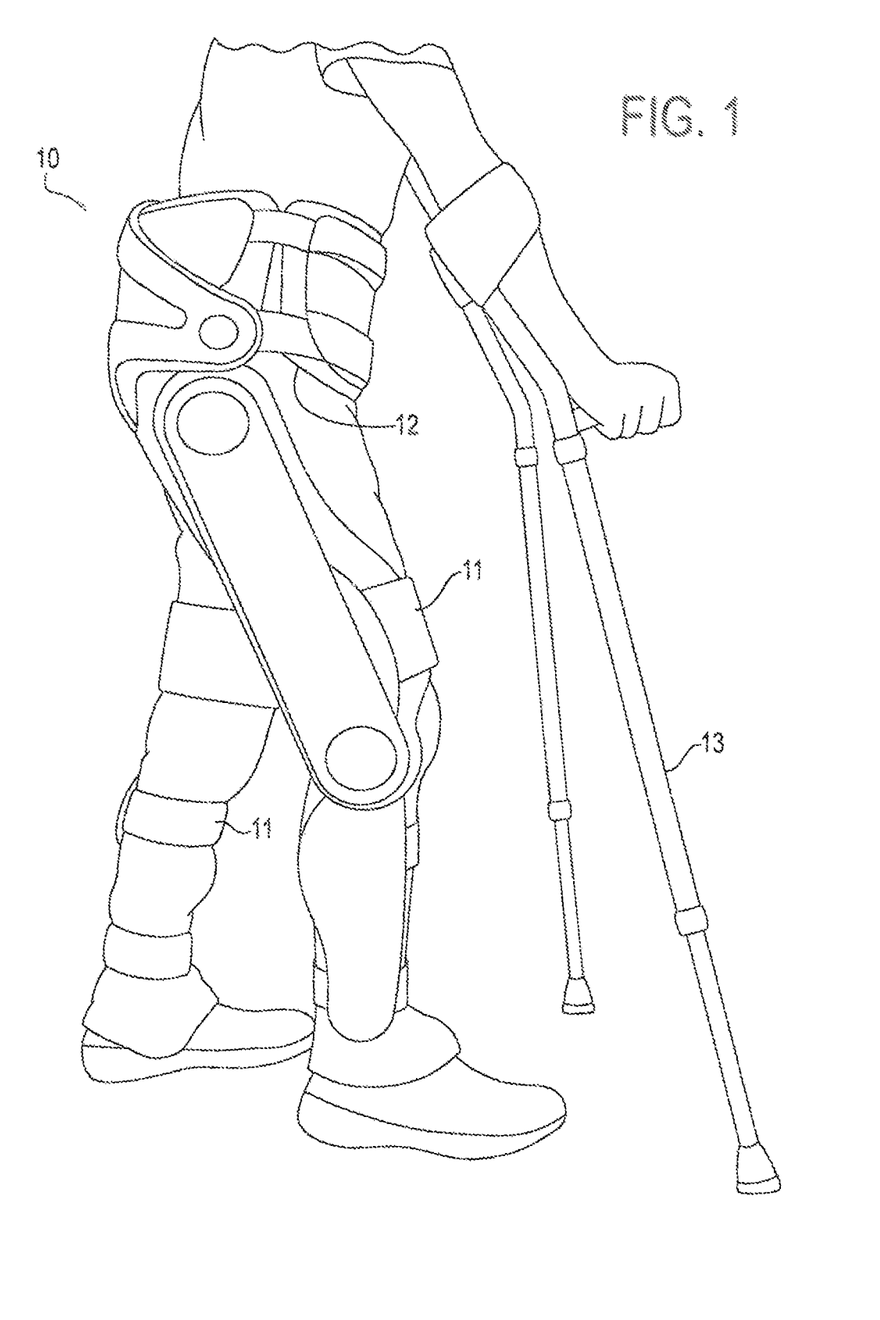
FIG. 1 is a drawing depicting an exemplary exoskeleton device as being worn by a user.

As shown in FIG. 1, an exoskeleton device 10, which also may be referred to in the art as a "wearable robotic device", can be worn by a user. To attach the device to the user, the device 10 can include attachment devices 11 for attachment of the device to the user via belts, loops, straps, or the like. Furthermore, for comfort of the user, the device 10 can include padding 12 disposed along any surface likely to come into contact with the user. The device 10 can be used with a stability aid 13, such as crutches, a walker, or the like.

Figure 2:
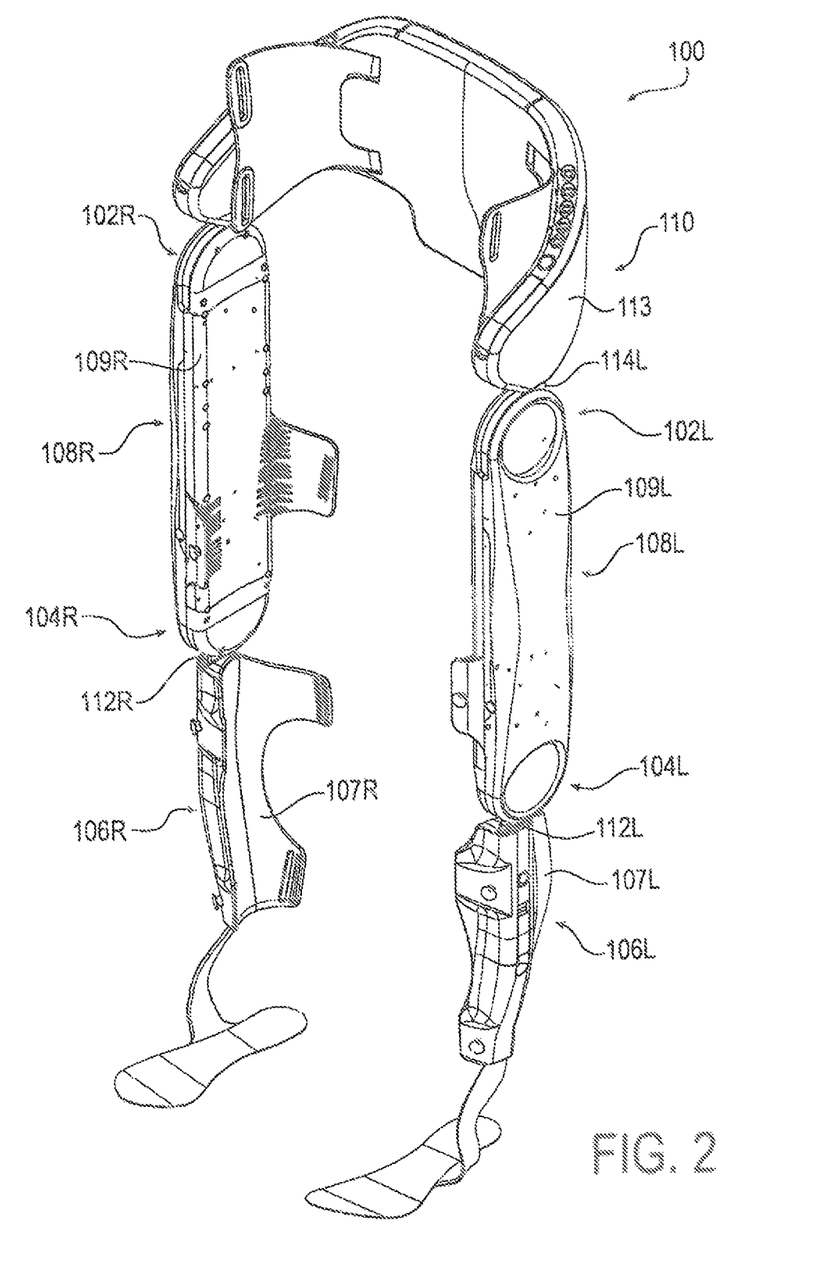
FIG. 2 is a drawing depicting a perspective view of an exemplary exoskeleton device in a standing position.
Figure 3:
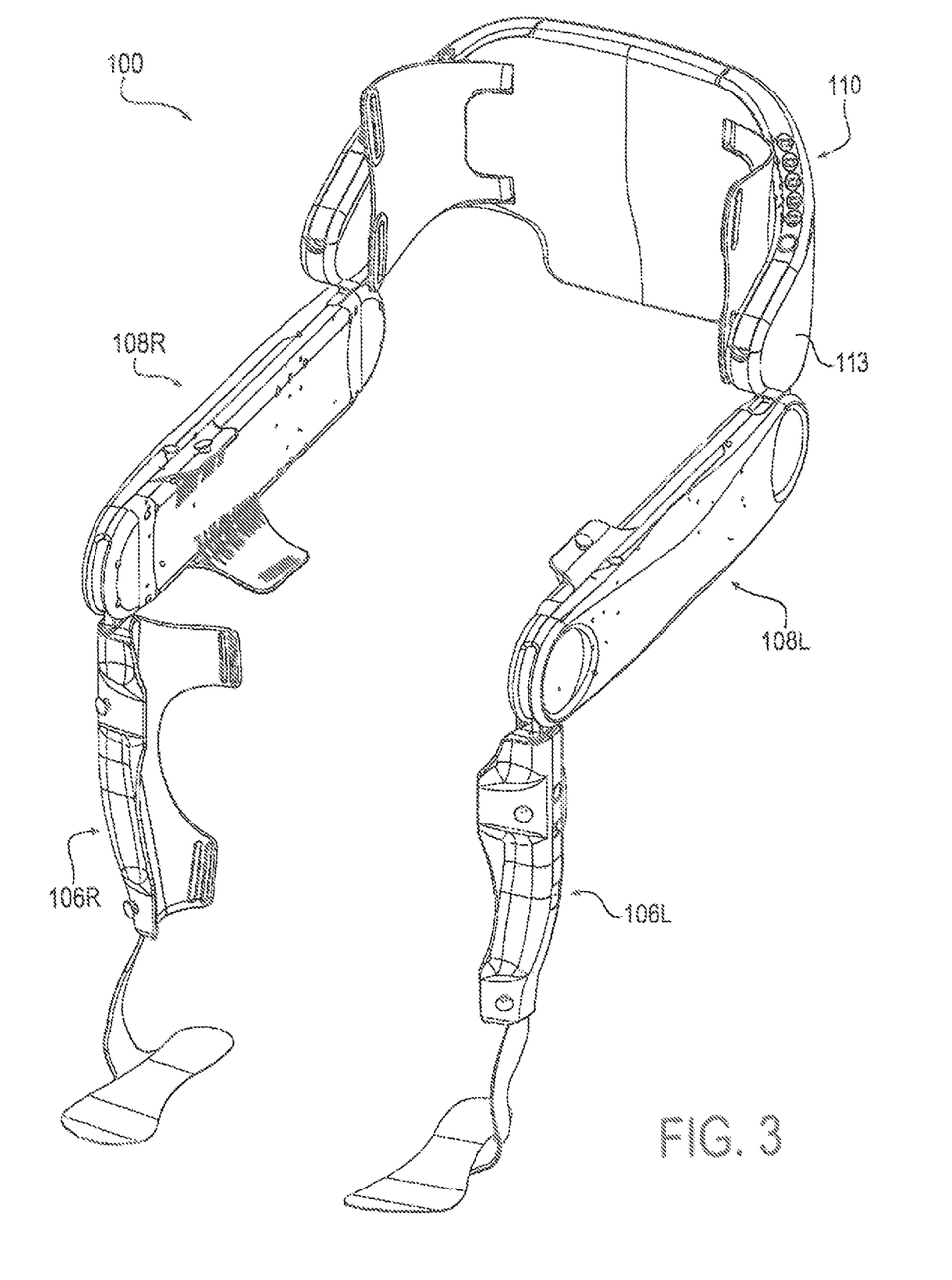
FIG. 3 is a drawing depicting a perspective view of the exemplary exoskeleton device in a seated position.
Figure 4:
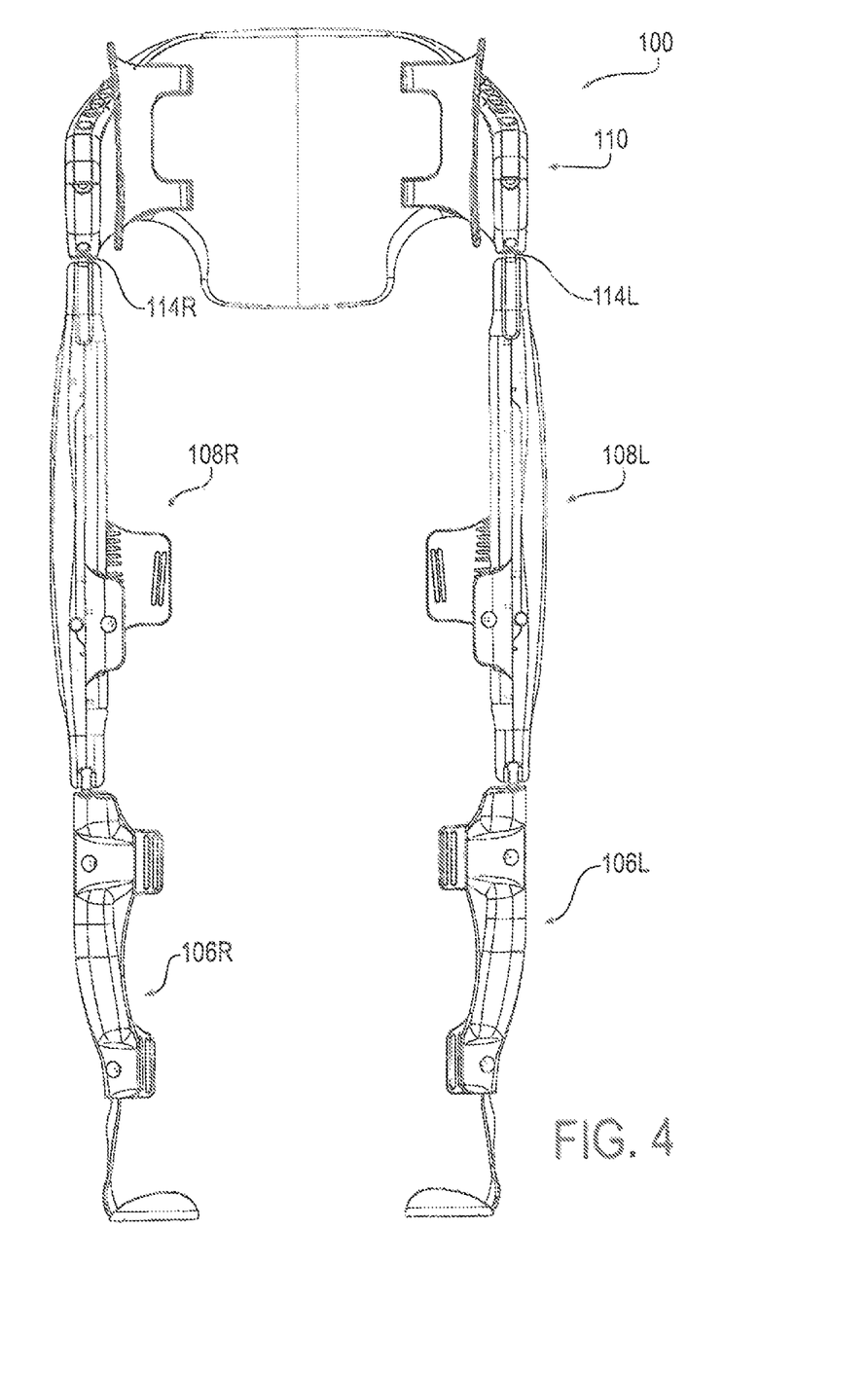
FIG. 4 is a drawing depicting a front view of the exemplary exoskeleton device in a standing position.
Figure 5:
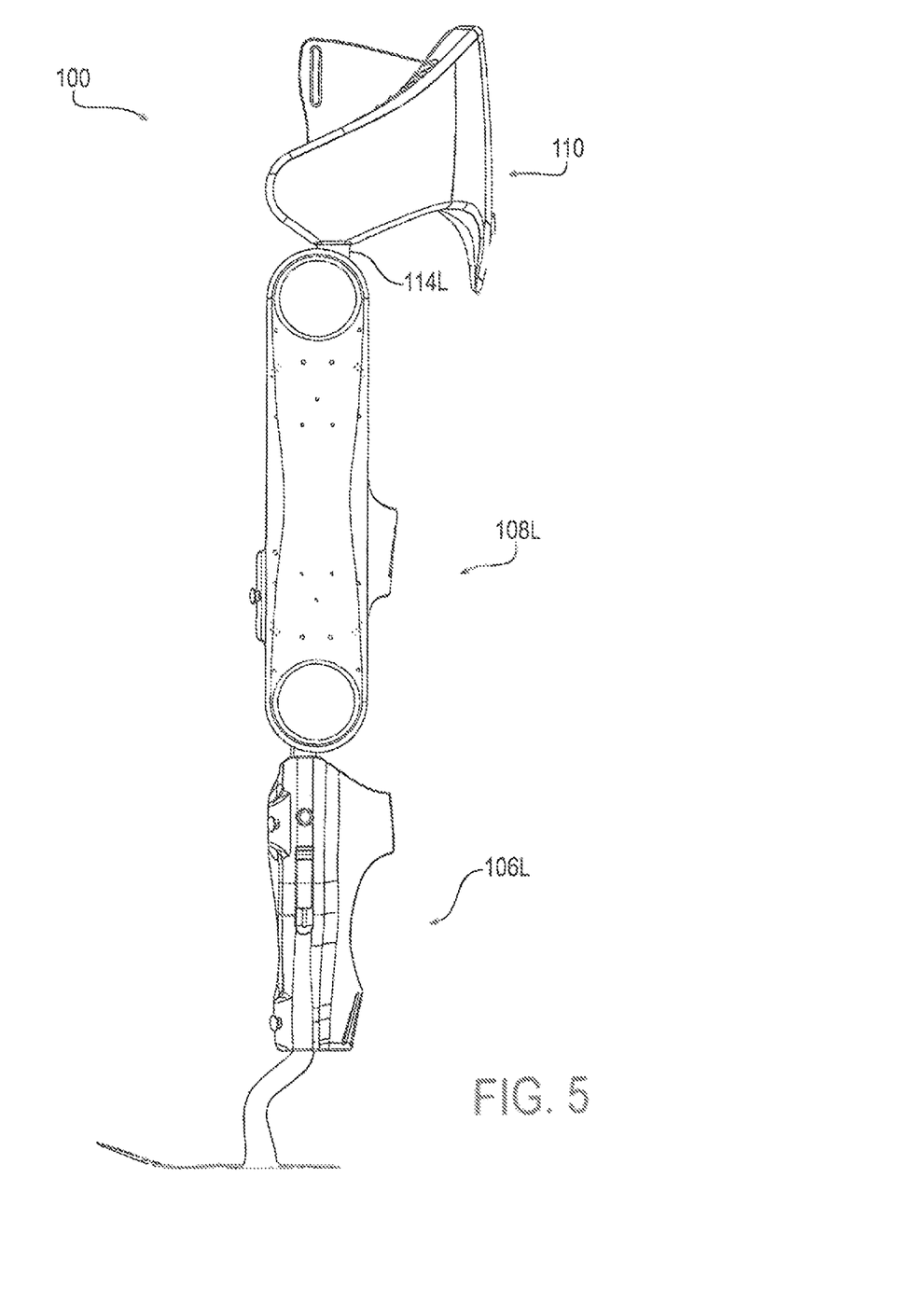
FIG. 5 is a drawing depicting a side view of the exemplary exoskeleton device in a standing position.
Figure 6:
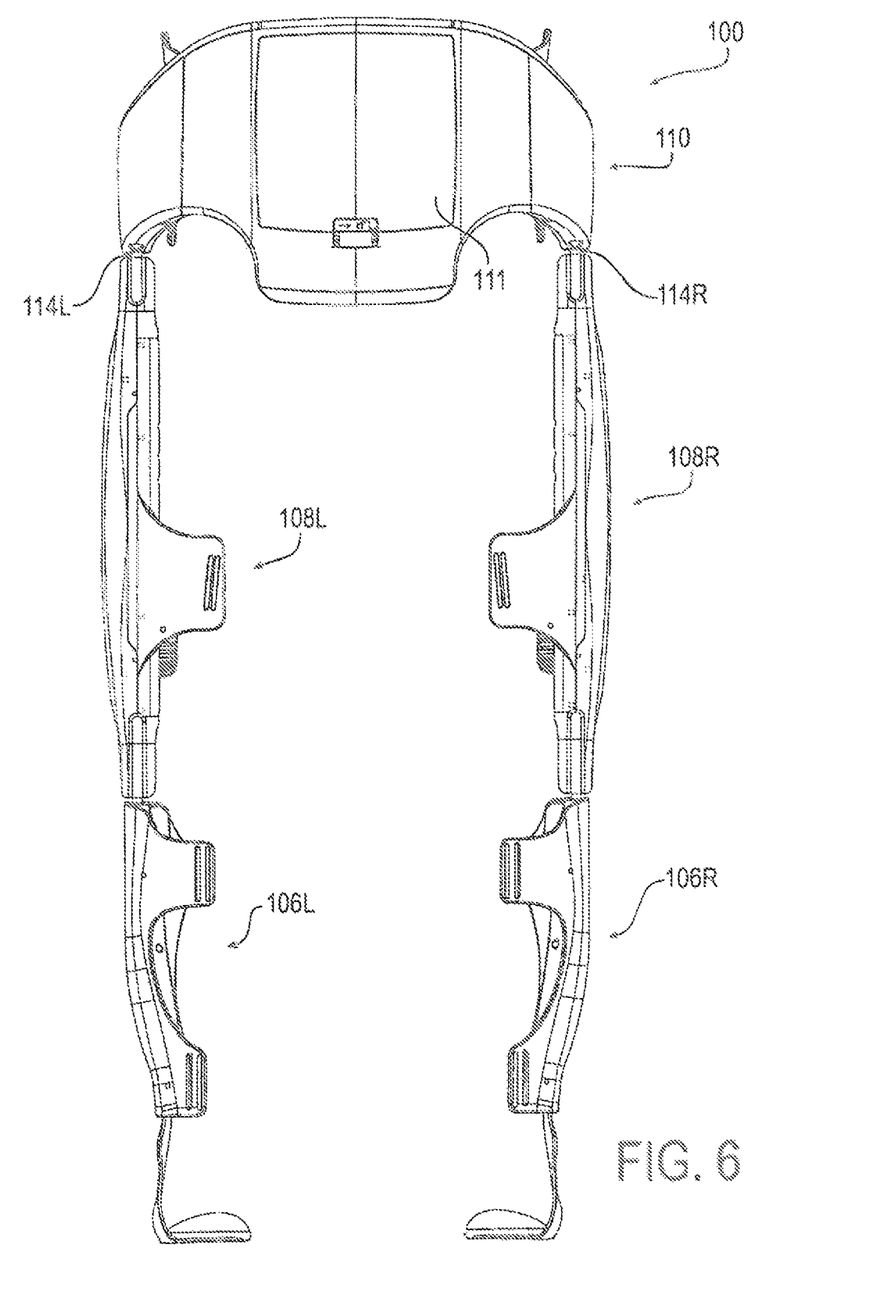
FIG. 6 is a drawing depicting a back view of the exemplary exoskeleton device in a standing position.

An exemplary legged mobility exoskeleton device is illustrated as a powered lower limb orthosis 100 in FIGS. 2-6. Specifically, the orthosis 100 shown in FIGS. 2-6 may incorporate four drive components configured as electromotive devices (for example, electric motors), which impose sagittal plane torques at each knee and hip joint components including (right and left) hip joint components 102R, 102L and knee joint components 104R, 104L. FIG. 2 shows the orthosis 100 in a standing position while FIG. 3 shows the orthosis 100 in a seated position.

As seen in the figures, the orthosis contains five assemblies or modules, although one or more of these modules may be omitted and further modules may be added (for example, arm modules), which are: two lower (right and left) leg assemblies (modules) 106R and 106L, two (left and right) thigh assemblies 108R and 108L, and one hip assembly 110. Each thigh assembly 108R and 108L includes a respective thigh assembly housing 109R and 109L, and link, connector, or coupler 112R and 112L extending from each of the knee joints 104R and 104L and configured for moving in accordance with the operation of the knee joints 104R and 104L to provide sagittal plane torque at the knee joints 104R and 104L.

The connectors 112R and 112L further may be configured for releasably mechanically coupling each of thigh assembly 108R and 108L to respective ones of the lower leg assemblies 106R and 106L. Furthermore, each thigh assembly 108R and 108L also includes a link, connector, or coupler 114R and 114L, respectively, extending from each of the hip joint components 102R and 102L and moving in accordance with the operation of the hip joint components 102R and 102L to provide sagittal plane torque at the knee joint components 104R and 104L. The connectors 114R and 114L further may be configured for releasably mechanically coupling each of thigh assemblies 108R and 108L to the hip assembly 110.

In some embodiments, the various components of device 100 can be dimensioned for the user. However, in other embodiments the components can be configured to accommodate a variety of users. For example, in some embodiments one or more extension elements can be disposed between the lower leg assemblies 106R and 106L and the thigh assemblies 108R and 108L to accommodate users with longer limbs. In other configurations, the lengths of the two lower leg assemblies 106R and 106L, two thigh assemblies 108R and 108L, and one hip assembly 110 can be adjustable. That is, thigh assembly housings 109R, 109L, the lower leg assembly housings 107R and 107L for the lower leg assemblies 106R, 106L, respectively, and the hip assembly housing 113 for the hip assembly 110 can be configured to allow the user or medical professional to adjust the length of these components in the field. For example, these components can include slidable or movable sections that can be held in one or more positions using screws, clips, or any other types of fasteners. In view of the foregoing, the two lower leg assemblies 106R and 106L, two thigh assemblies 108R and 108L, and one hip assembly 110 can form a modular system allowing for one or more of the components of the orthosis 100 to be selectively replaced and for allowing an orthosis to be created for a user without requiring customized components. Such modularity can also greatly facilitate the procedure for donning and doffing the device.

In orthosis 100, each thigh assembly housing 109R, 109L may include substantially all the drive components for operating and driving corresponding ones of the knee joint components 104R, 104L and the hip joint components 102R, 102L. In particular, each of thigh assembly housings 109R, 109L may include drive components configured as two motive devices (e.g., electric motors) which are used to drive the hip and knee joint component articulations. However, the various embodiments are not limited in this regard, and some drive components can be located in the hip assembly 110 and/or the lower leg assemblies 106R, 106L.

A battery 111 for providing power to the orthosis can be located within hip assembly housing 113 and connectors 114R and 114L can also provide means for connecting the battery 111 to any drive components within either of thigh assemblies 108R and 108L. For example, the connectors 114R and 114L can include wires, contacts, or any other types of electrical elements for electrically connecting battery 111 to electrically powered components in thigh assemblies 108R and 108L. In the various embodiments, the placement of battery 111 is not limited to being within hip assembly housing 113. Rather, the battery can be one or more batteries located within any of the assemblies of orthosis 100.

The referenced drive components may incorporate suitable sensors and related internal electronic controller or control devices for use in control of the exoskeleton device. Such internal control devices may operate using the sensory information from the detection of postural cues, by which the internal control device will automatically cause the exoskeleton device to enter generalized modes of operation, such as sitting, standing, walking, variable assist operation, and transitions between these generalized modes or states (e.g., Sit to Stand, Stand to Walk, Walk to Stand, Stand to Sit, etc.) and step transition (e.g., Right Step, Left Step). The internal electronic control devices further may perform fall mitigation and recovery operations for the exoskeleton device, as described for example in Applicant's International Patent Appl. No. PCT/US2016/016319 filed on Feb. 3, 2016, which is incorporated here in its entirety by reference.

The internal electronic control devices and related electronics further may incorporate or include a mobility assistance device communications interface that is configured to transmit and receive signals over an electronic signal interface. In exemplary embodiments, the mobility device communications interface may communicate electronically over a wireless interface by transmitting signals to and receiving signals from a communications interface of an electronic communication device including a control application for controlling the drive components of the mobility device.

To perform such operations, the drive systems and internal control device of the mobility assistance device may employ the use of accelerometers, gyroscopes, inertial measurement, and other sensors to detect and observe the upper leg, hip, and knee orientations, angles, and/or angular velocities. The internal control device may then selectively control the drive components to modulate the joint components, and particularly the knee and hip joint components, to apply torque, implement locked or released states, or otherwise effect positioning or movement of the joint components to control the exoskeleton device for modes operation or for fall mitigation.

To implement the features of the present invention, the exoskeleton device or other mobility device may include a control system having one or more processor devices that are configured to execute program code stored on a non-transitory computer readable medium embodying the control methods associated with the generalized control of the exoskeleton device, including the control operations of the present invention. It will be apparent to a person having ordinary skill in the art of computer programming of electronic devices how to program the electronic control device to operate and carry out logical functions associated with present invention. Accordingly, details as to specific programming code have been left out for the sake of brevity. Also, controller functionality could be carried out via dedicated hardware, firmware, software, or any combinations thereof, without departing from the scope of the invention.

As will be understood by one of ordinary skill in the art, therefore, the control system may have various implementations. For example, the control system may be configured as any suitable processor device, such as a programmable circuit, integrated circuit, memory and I/O circuits, an application specific integrated circuit, microcontroller, complex programmable logic device, other programmable circuits, or the like. The control system may also include a non-transitory computer readable medium, such as random access memory (RAM), a read-only memory (ROM), an erasable programmable read-only memory (EPROM or Flash memory), or any other suitable medium. Instructions for performing the methods described below may be stored in the non-transitory computer readable medium and executed by the processor device.

Figure 7:
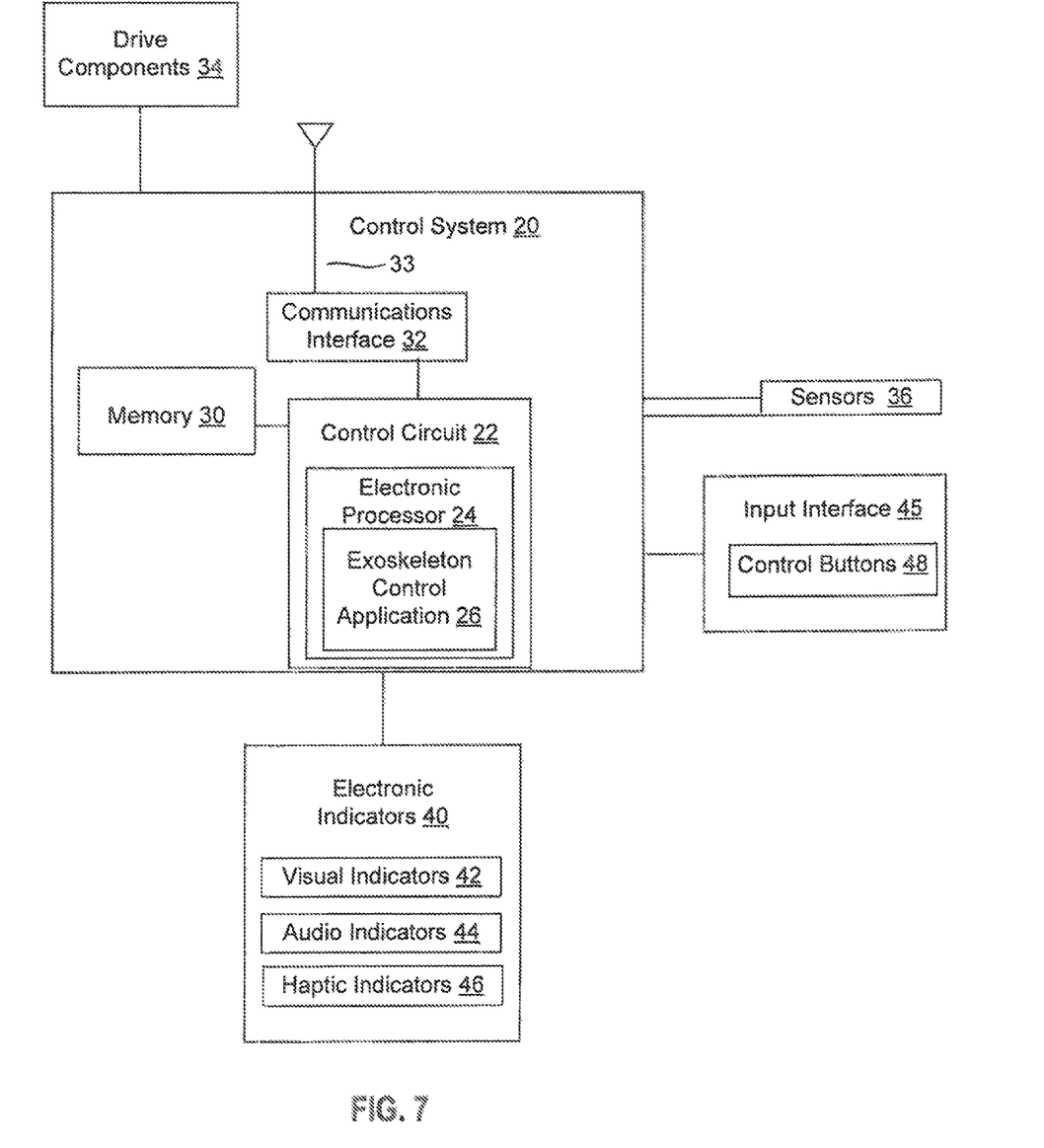
FIG. 7 is a drawing depicting a schematic block diagram of operative portions of an exemplary control system and related electronic components of a mobility device in accordance with embodiments of the present invention.

FIG. 7 is a drawing depicting a schematic block diagram of operative portions of an exemplary control system 20 and related electronic components in accordance with embodiments of the present invention, that is a component of the mobility assistance device such as the exoskeleton device of the previous figures. The control system 20 may include a primary control circuit 22 that is configured to carry out various control operations relating to control of the exoskeleton device. The control circuit 22 may include an electronic processor 24, such as a CPU, microcontroller or microprocessor. Among their functions, to implement the features of the present invention, the control circuit 22 and/or electronic processor 24 may comprise an electronic controller that may execute program code embodied as the exoskeleton control application 26. It will be apparent to a person having ordinary skill in the art of computer programming, and specifically in application programming for electronic and communication devices, how to program the device to operate and carry out logical functions associated with application 26. Accordingly, details as to specific programming code have been left out for the sake of brevity.

The exoskeleton control application 26 may be stored in a non-transitory computer readable medium, such as random access memory (RAM), a read-only memory (ROM), an erasable programmable read-only memory (EPROM or Flash memory), or any other suitable medium. In the example of FIG. 7, the exoskeleton control application 26 is shown as being stored internally within the processing components, but the application also may be stored in an additional memory device such as the memory 30. Instructions for performing the methods described below that are stored in the non-transitory computer readable medium may be executed by the processor components 22 and 24. Also, while the code may be executed by control circuit 22 or processor 24 in accordance with an exemplary embodiment, such controller functionality could also be carried out via dedicated hardware, firmware, software, or combinations thereof, without departing from the scope of the invention.

The control system 20 may constitute internal electronic control devices and related electronics incorporated into one or more of the exoskeleton device components, and typically may be incorporated into one or more of the thigh assembly or hip assembly components of the exoskeleton device. The control system 20 further may include a communications interface 32 for electronic communication with components external to the control system. For example, the communications interface may provide for electronic communication via an antenna 33 with an external mobile communication device, and thus may be configured to transmit and receive signals over an electronic signal interface. In exemplary embodiments, the communications interface may communicate electronically with an external mobile communication device over a wireless interface by transmitting signals to and receiving signals from the drive components for control of the mobility device. A mobile communications device and related control systems and methods are disclosed Applicant's International Patent Appl. No. PCT/US2016/40304 filed on Jun. 30, 2016, which is incorporated here in its entirety by reference.

The control system 20 further may be in electronic communication with both sensory and drive components of the exoskeleton device. The connections may be hard wired connections via internal circuit boards and other wired connections, but wireless communication also may be employed between the control system and/or sensor and drive components. In FIG. 7 the drive components are generally indicated by block 34, and the sensors are generally indicated by block 36. For gathering appropriate sensory information, the sensors 36 may include the use of accelerometers, gyroscopes, inertial measurement, and other sensors to detect and observe the upper leg and torso orientation or angle and angular velocity. Example sensors may include hall effect sensors, magnetic angle sensors, accelerometer sensors, gyroscope sensors, resistance temperature detectors, and others. There also may be one or more redundant sensors that correspond respectively to one or more of the above sensors, and the redundant sensors may provide sensor information when there is a sensor fault detected in a respective sensor.

The control system 20 may then selectively control the drive components 34 to configure and modulate the joint components of the exoskeleton device, and particularly the knee and hip joint components, to apply torque, implement locked or released states, or otherwise effect positioning or movement of the joint components for control of the exoskeleton device for various modes of operation and for fall mitigation.

As described for example in Applicant's referenced previous patent applications, in the described exoskeleton device operation generally is automated based on sensory detections. As an example, to go from sit to stand a user may pull in the legs and lean forward, as any person normally does when getting ready to stand. Upon sensing such a pre-standing position, the exoskeleton drive system would send a haptic feedback signal to the user, such as a vibration indicator, informing the user that a transition to standing will occur. Control of mobility mode of operation (sit, stand, walk, etc.), and transitions between mobility modes, proceeds as warranted. Mode transitions and mode operations, therefore, are operated generally by the sensors reading user postural cues, which are interpreted by the control system that in turn generates control signals to drive operation of the drive components.

The control system 20 further may be in electronic communication with a plurality of electronic indicators 40. In FIG. 7, the electronic indicators are generally indicated by block 40. The electronic indicators may include visual indicators 42 that indicate aspects of device state and operation by lighting. In exemplary embodiments, the lighting may be color-coded lighting in which light emitting diodes (LEDs) are employed as the visual indicators. The electronic indicators further may include audio indicators 44, by which speakers may be employed to provide audio alerts pertaining to aspects of device state and operation. Different sounds may be employed for different types of audio alerts, and may be used in combination with the visual indicators 42 to provide multiple indicator combinations corresponding to information pertaining to different aspects of device state and operation. The electronic indicators further may include haptic indicators 46. The haptic indicators 46 may be configured as vibration generators that provide vibration indications as alerts pertaining to aspects of device state and operation.

The control system 20 further may be in electronic communication with an input interface 45. The input interface may be configured as an electronic control panel on the exoskeleton device that permits user inputs for control of the exoskeleton device. The input interface may include one or more control buttons 48 that may provide a varied array of control options for a user, including a power button for turning on and enabling the exoskeleton device.

The described exoskeleton device can be controlled in a manner that performs advanced gait control as further described below. The control methods of the present invention may be performed by the control system 20, for example via the processor components control circuit 22 and/or processor 24, executing the program code embodying the exoskeleton control application 26 stored on a non-transitory computer readable medium. In general, therefore, aspects of the invention are directed to enhanced methods of controlling a mobility device having a plurality of mobility device components including at least one actuator component that drives at least one joint component, as well as a plurality of sensors to detect a state of the at least actuator component and joint component. Although the exemplary control methods are described below as a specific order of executing functional logic steps, the order of executing the steps may be changed relative to the order described. Also, two or more steps described in succession may be executed concurrently or with partial concurrence. It is understood that all such variations are within the scope of the present invention.

For explanation of the methods of advanced gait control, the following terminology is used. A leg is in a stance state when such leg is planted with the foot supported on the ground and not stepping. A leg is in a swing state when the leg is not planted on the ground and is moving dynamically, such as during stepping. A gait cycle is a repeating series of stepping motions in which the legs are alternating between stance support states and dynamic swing states.

During standard gait control, the stepping states are separated by double support stance states in which both legs are in the stance state and not moving (e.g., both legs are static in stance state and may be supported on the ground), and the duration of such a double support static state is referred to as the dwell time. From a perspective of operation of an exoskeleton device, a "double support state" is defined as a static period in which the exoskeleton device is at rest, such as between stepping motions and/or single support states, in which both of the user's feet typically are on the ground. From a perspective of operation of an exoskeleton device, a "single support state" is defined as a dynamic period in which the exoskeleton device is in motion, such as between standing positions and/or double support states, or between stepping motions and/or single support states of the opposite leg, in which only one of the user's feet typically is on the ground. As further described below, the advanced gait control of the present invention operates to substantially reduce or eliminate the double support states, thereby minimizing the dwell time. During a single support state, stepping is typically occurring whereby one leg is in a stance state while the opposite leg is moving in a dynamic swing state. Accordingly, a stepping state also is referred to as a dynamic single support state.

During the gait cycle, one leg tends to be rearward relative to the opposite leg in the stepping direction. The rearward leg is referred to as the trailing leg with the opposite leg being referred to as the forward leg. During stepping, the stance leg becomes the trailing leg with the swing leg swinging or moving to the forward leg position. Accordingly, the stance leg during stepping also is referred to as the stance/trailing leg.

In the advanced gait control of the present invention, at least one of an angular position or angular velocity of the stance/trailing leg is sensed and measured during single support dynamic states to determine whether advanced gait will occur during the following step, e.g., the angle of the left leg is sensed and measured during a right step to determine if advanced gait should occur during the subsequent left step. Advanced gait is enabled if the angular position or angular velocity of the stance/trailing leg surpasses a threshold during the dynamic single support state, referred to herein as the "advanced gait threshold", which may be manually or automatically set by a user or clinician. Angular velocity predominantly is related to continuous hip motion, whereas angular position is more predominantly related to continuous knee motion. The reliance on angular position (as related to continuous knee motion) and angular velocity (as related to continuous hip motion) may be implemented as two separate advanced gait thresholds or a common advanced gait threshold with the two parameters operating in tandem. In setting the advanced gait threshold(s) in a clinical setting, the advanced gait threshold initially would be set very high so as to render a switch from standard gait control to advanced gait control improbable. The threshold setting would then progressively be lowered to reach a point relative to the user's capabilities at which the switch to advanced gait control is suited to such user. In this manner, the switch from standard gait control to advanced gait control is made safely and in line with clinical capabilities and performance goals of the user.

The joint angle relative to a center line of the user constitutes a tilt angle by which the angular positioning of the stance/trailing leg is assessed. The trailing leg angle is tracked between mid-stance to terminal stance portions of the stance state, with the trailing leg in the single support state as the opposite leg swings. This differs from the standard gait, in which stepping occurs based on measurements of the landing or forward leg (not the trailing leg) while in a double support static state. The advanced gait threshold will tend to differ among different users, and is set based on multiple criteria including, for example, user size, step length, and step speed capabilities. The sensors for measuring the joint angles preferably are installed within the thigh or upper leg component of the exoskeleton device.

When the advanced gait threshold is satisfied and thus advanced gait control has been enabled, an advanced gait step will occur immediately following the observed step. When the advanced gait threshold is not satisfied and thus advanced gait control has not been enabled, a minimum delay or dwell time may occur thereby creating a double support state, after which steps may be triggered in the double support state comparably as the conventional standard gait control. In exemplary embodiments, the angular position of the leading leg further may be observed in the double support stance state to determine when standard gait will occur for the following step. At this point, exemplary control may enable advanced gait control only after the following step provided the advanced gait threshold is satisfied, thereby enabling advanced gait during stepping. In an exemplary embodiment, for an added safety feature or as a precaution, to avoid unintentional transitions into advanced gait control, continuous motion will not occur until the conditions for advanced gait, i.e. satisfying the advanced gait threshold, have been met on two or more consecutive standard gait steps.

By employing the operation above by which advanced gait control is triggered by satisfaction of the advanced gait threshold, double support state delays or dwell time may be substantially reduced or eliminated, thereby reducing the "clunkiness" of stepping experienced in conventional configurations that employ only the standard gait control. Accordingly, an advantage of the advanced gait control is to substantially reduce or eliminate the dwell time for a smoother gait. To achieve a more continuous motion, at least one joint should be moving at any given time. That is, even if the delay between steps is substantially reduced or eliminated, motion will not be continuous if all joints come to rest at the beginning and end of those steps as has typically been done in conventional standard gate control.

Accordingly, to enable continuous motion, the advanced gait control utilizes joint trajectories in which joint velocities are non-zero for the hip joint during the transitions from swing to stance states, and non-zero for the knee joint during the transition from stance to swing states. In this manner, joint trajectories during advanced gait control start during the swing state for the hip joint, and start during stance state for the knee joint. If an advanced gait trajectory is utilized during hip joint swing, it will be followed by an advanced gait trajectory in hip joint stance. In other words, advanced gait is not utilized for hip stance unless preceded by advanced gait during hip swing. Similarly, if an advanced gait trajectory is utilized during knee stance, advanced gait trajectory in turn will be employed in knee swing, and advanced gait is not utilized for knee swing unless preceded by advanced gait during knee stance. Once an advanced gait trajectory has been utilized for either the hip joint in the swing state, or the knee joint in the stance state, advanced gait control is employed in the subsequent hip stance or knee swing states respectively, regardless of any intervening delay. This is done to ensure that joint trajectories are substantially continuous to minimize disruptive motions.

Once advanced gait control has been enabled, steps potentially occur in immediate succession, with each step blending into the next by way of hip swing-to-stance extension, and/or knee stance-to-swing flexion. To transition back to standard gait, the user no longer satisfies the advanced gait threshold during a given step. In relation to joint measurements, this means maintaining the angular position of the stance leg during a given step, such that the angular position does not satisfy the advanced gait threshold to continue with advance gate control. For example, if a right step is being taken (right leg swing, left leg stance), then the user can arrest forward motion (e.g., by using a stability aid) as the left leg extends such that the left leg does not rotate relative to the ground, and thereby does not surpass the advanced gait threshold during that step. To facilitate the transition from advanced gait control to standard gait control, the control system decision to utilize advanced gait during knee stance is delayed until right before terminal stance knee flexion would occur, which occurs at approximately 80% stance. If the user is not beyond the advanced gait threshold at this point, even if the user exceeded the advanced gait threshold previously during that stance state, advanced gait will not be utilized at the knee joint. With such control being based on knee joint measurements and states, it has been observed that unintentional use of advanced gait control during hip joint swing is not typically disruptive.

Figure 8:
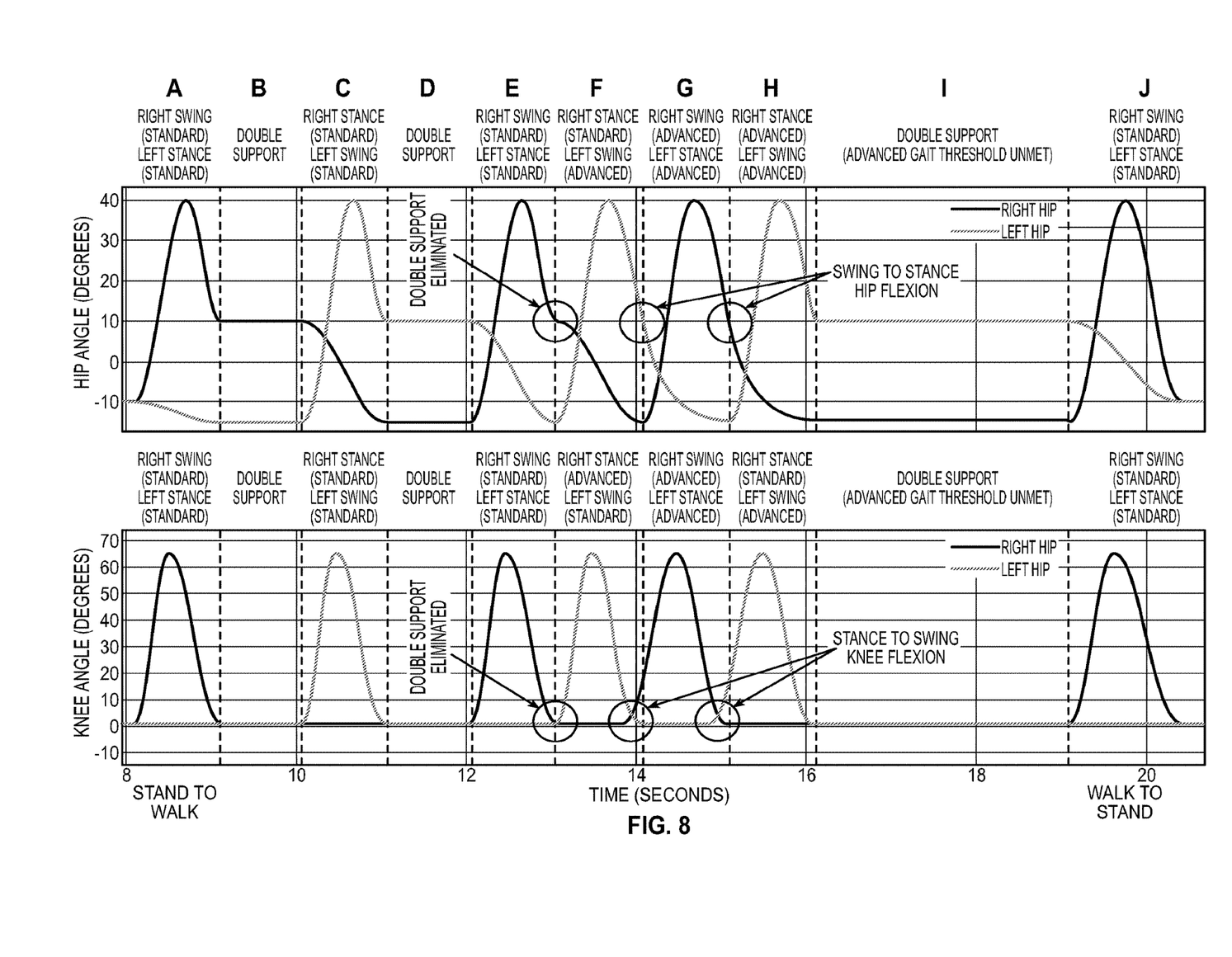
FIG. 8 is a graphical depiction of hip joint component angle versus time across different gait stages for both the right hip joint component and left hip joint component of the exoskeleton device, and a corresponding graphical depiction of knee joint component angle versus time across such different gait stages for the right knee joint component and left knee joint component of an exoskeleton device.

FIG. 8 is a graphical depiction of hip joint component angle versus time across different gait stages for both the right hip joint and left hip joint of the exoskeleton device, and a corresponding graphical depiction of knee joint component angle versus time across such different gait stages for the right knee joint and left knee joint of the exoskeleton device. Panels A-J correspond to different gait stages. For purposes of illustration, a subject starts in a standard gait mode with the left leg in stance state and the right leg in swing state, and thus the angles of the hip and knee joints alter as shown in Panel A as the right leg swings. In standard gait control, the subject follows the swing state of the right leg of Panel A with a static double support state as shown in Panel B, during which the hip and knee joint angles are constant as motion comes to a stop. Panels C and D show similar gait characteristics of the standard gait control with the right leg now in the stance state in the left leg now in swing state (Panel C) followed by another static double support stance state (Panel D). Panel E then is comparable to Panel A illustrating the next step, which is the next gait cycle in which the left leg again is in the stance state with the right leg in the swing state. As referenced above, the standard gait control is characterized by significant time spent in the static double support states of Panels B and D during which the joint angle velocities are zero.

The transition from Panel E to Panel F corresponds to transitioning from standard gait control to advanced gait control. To achieve such transition, an angular position of the stance/trailing leg is sensed and measured during the dynamic single support states to determine whether advanced gait will occur during the following step, e.g., corresponding to Panel E the angle of the left leg, as the stance/trailing leg, is sensed and measured during a right step (right leg swing) to determine if advanced gait should occur during the subsequent left step. Advanced gait control is enabled if the angular position of the stance/trailing leg surpasses the advanced gait threshold, and an advanced gait step occurs immediately following the observed step.

Panels F, G, and H of FIG. 8 illustrate advanced gait control steps. Looking at the hip angle progression during advanced gate control, there is a swing to stance hip joint extension, i.e., the hip joint component of the exoskeleton device extends as the corresponding leg transitions from the swing state to the stance state. In this manner, the hip joint component experiences a continuous velocity through the heel strike. Correspondingly, looking at the knee angle progression during advanced gate control, there is a stance to swing knee joint flexion, i.e., the knee joint component of the exoskeleton device flexes as the corresponding leg transitions from the stance state to the swing state. In this manner, the knee joint flexes early in the swing state, or in other words, essentially the knee begins bending toward the end of stance state to get a better "push off" in the step at the initiation of the swing state. The result of the advanced gait control is a more continuous stepping motion, which significantly reduces or eliminates the double support static states experienced in the standard gait control steps as shown in Panels B and D.

Panels I and J demonstrate a transition back from the advanced gait control to standard gait control. In the transition of Panel H to Panel I, the angle measurements have transitioned to a state in which the advanced gait threshold is no longer satisfied. As a result, the system returns to the double support static state in preparation to resume walking in accordance with standard gait control, with a standard gait step being taken as depicted in Panel J.

In one aspect of advanced gait control, the system optimizes user contribution to stepping versus contribution by the exoskeleton device. For users who are not wholly disabled, adjusting the user contribution to require more or less effort can help the user train with the device, and improve overall strength and performance. To achieve such control, the exoskeleton joint components are back drivable to accommodate force applied by the user's own efforts to walk.

In an exemplary embodiment, step length may be tied to step speed, giving the user the ability to speed and slow the gait as desired. In this manner, a user can by choice switch between standard gait control and advanced gait control. For example, a user can perform with the exoskeleton device to satisfy the advanced gait threshold, thereby entering advanced gait control from standard gait control. To switch back to standard gait control from advanced gait control, the user can hold the stance/trailing leg in place to resume a double support stance, which then triggers the system to transition back to standard gait control. Such transition is depicted, for example, in the extended double support static state of Panel I of FIG. 8, after which the standard gait control is resumed.

Another feature of advanced gait control is an automated speed boost feature. One exemplary device setting related to such feature is a "Speed Boost Level" feature, which automatically increases step speed while performing in the advanced gait mode. A "high" setting will increase step speed by a full increment (i.e. "medium" speed steps in standard gait will become fast speed steps in advanced gait). The "low" setting will increase step speed by a half increment (i.e. "low" speed steps in standard gait will become "medium-low" speed steps in advanced gait). Another exemplary device setting for automated speed boost is a "Speed Boost Onset" feature, which determines how the speed boost will occur. With a "gradual" onset setting, the speed boost level occurs incrementally, over the course of a few advanced gait steps. With an "immediate" onset setting, the speed boost level will occur immediately, with the first advanced gait step.

An aspect of the invention, therefore, is a control method for a mobility assistance device employing advanced gait control. In exemplary embodiments, the control method employs the following steps: providing said mobility device including a control system for controlling operation of the mobility device components to selectively configure and modulate hip and knee joint components to perform a gait cycle; providing within said mobility device a control application to be executed by the control system to control the gait cycle; and providing within said mobility device a plurality of sensors to detect a state of the hip and knee joint components to determine an angular position of the right leg and left leg during the gait cycle. The control system executes the control application to perform the steps of: sensing at least one of an angular position or angular velocity of a stance/trailing leg during a single support dynamic state of the gait cycle; determining whether the angular position or angular velocity satisfies an advanced gait threshold; and when it is determined that the angular position or angular velocity satisfies the advanced gait threshold, the control system employs advanced gait control of the hip and knee joint components by which a duration of double support states between single support dynamic states is minimized.

For advanced gait control the control system further controls the hip joint components to utilize advanced gait joint trajectories in which hip joint component velocities are non-zero for the hip joint components during transitions from swing states to stance states of the gait cycle, and in which knee joint component velocities are non-zero for the knee joint components during transitions from stance states to swing states of the gait cycle. In this manner, the control system controls the knee and hip joint components such that each step of the gait cycle blends into a next step by way of hip joint component swing-to-stance extension and/or knee joint component stance-to-swing flexion, and at least one joint component is always moving during the gait cycle. When it is determined that the angular position and angular velocity do not satisfy the advanced gait threshold, the control system employs standard gait control in which double support states are maintained between single support dynamic states, and a decision whether to step is made by sensing an angular position of the forward leg during the double support states.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A control method of controlling a mobility device having a plurality of mobility device components including a right hip joint component and a right knee joint component corresponding to a right leg, and a left hip joint component and a left knee joint component corresponding to a left leg, the control method comprising the steps of:
providing said mobility device, said mobility device further including a control system for controlling operation of the mobility device components to selectively control the hip and knee joint components to perform a gait cycle;
wherein the selective control comprises controlling the hip joint components through a hip joint component trajectory of varying hip joint component angle and hip joint component velocity, and controlling the knee joint components through a knee joint component trajectory of varying knee joint component angle and knee joint component velocity;
providing within said mobility device a control application to be executed by the control system to control the gait cycle;
providing within said mobility device a plurality of sensors to detect a state of the hip and knee joint components to determine an angular position of the right leg and left leg during the gait cycle; and
executing the control application with the control system further to perform the steps of:
sensing at least one of an angular position or an angular velocity of a stance leg during stepping during a single support dynamic state of the gait cycle comprising a stepping state in which one leg is swinging while the opposing leg is the stance leg during stepping;
determining whether the angular position or angular velocity surpasses an advanced gait threshold; and
when it is determined that the angular position or angular velocity surpasses the advanced gait threshold, the control system employs advanced gait control of the hip and knee joint components whereby a determination to initiate stepping is made during the single support dynamic state,
the advanced gait control comprising controlling the hip joint components and knee joint components through the hip joint trajectory and the knee joint trajectory corresponding to advanced gait trajectories to perform a stepping motion in which steps are taken in immediate succession thereby minimizing a duration of double support states in which both legs are in stance between single support dynamic states.

2. The control method of claim 1, wherein for advanced gait control the control system controls the hip joint components to utilize advanced gait joint trajectories in which hip joint component velocities are non-zero for the hip joint components during transitions from swing states to stance states of the gait cycle.

3. The control method of claim 1, wherein for advanced gait control the control system controls the knee joint components to utilize advanced gait joint trajectories in which knee joint component velocities are non-zero for the knee joint components during transitions from stance states to swing states of the gait cycle.

4. The control method of claim 2, wherein when an advanced gait trajectory is utilized during hip joint component swing, the control system employs an advanced gait trajectory in a subsequent hip joint component stance.

5. The control method of claim 3, wherein when an advanced gait trajectory is utilized during knee joint component stance, the control system employs an advanced gait trajectory in a subsequent knee joint component swing.

6. The control method of claim 1, wherein for advanced gait control the control system controls the knee and hip joint components such that each step of the gait cycle occurs in immediate succession following a previous step by way of hip joint component swing-to-stance extension, and/or knee joint component stance-to-swing flexion.

7. The control method of claim 1, wherein the angular position is measured of a left stance leg during stepping during a single support dynamic state of the gait cycle to determine whether to take a step with the right leg, and the angular position is measured of a right stance leg during stepping during a single support dynamic state of the gait cycle to determine whether to take a step with the left leg.

8. The control method of claim 1, wherein the angular position of the stance leg during stepping is sensed between mid-stance to terminal stance of said stance leg during stepping.

9. The control method of claim 1, wherein when it is determined that the advanced gait threshold condition is not satisfied, the control system employs standard gait control in which double support states are maintained between single support dynamic states, and a decision whether to step is made by sensing an angular position of the forward leg during the double support state.

10. A non-transitory computer readable medium storing program code for a control application for use in controlling a mobility device including a plurality of mobility device components including a right hip joint component and a right knee joint component corresponding to a right leg, and a left hip joint component and a left knee joint component corresponding to a left leg;

wherein the mobility device further comprises: an electronic control system that executes the control application for controlling operation of the mobility device components to selectively control the hip and knee joint components to perform a gait cycle, wherein the selective control comprises controlling the hip joint components through a hip joint component trajectory of varying hip joint component angle and hip joint component velocity, and controlling the knee joint components through a knee joint component trajectory of varying knee joint component angle and knee joint component velocity, and a plurality of sensors to detect a state of the hip and knee joint components to determine an angular position of the right leg and left leg during the gait cycle; and the program code of the control application when executed by the electronic control system performs the steps of:

sensing at least one of an angular position or an angular velocity of a stance leg during stepping during a single support dynamic state of the gait cycle comprising a stepping state in which one leg is swinging while the opposing leg is the stance leg during stepping;

determining whether the angular position or angular velocity surpasses an advanced gait threshold; and when it is determined that the angular position or angular velocity surpasses the advanced gait threshold, the control system employs advanced gait control of the hip and knee joint components whereby a determination to initiate stepping is made during the single support dynamic state, the advanced gait control comprising controlling the hip joint components and knee joint components through the hip joint trajectory and the knee joint trajectory corresponding to advanced gait trajectories to perform a stepping motion in which steps are taken in immediate succession thereby minimizing a duration of double support states in which both legs are in stance between single support dynamic states.

11. The non-transitory computer readable medium of claim 10, wherein for advanced gait control the control system executes the program code to control the hip joint components to utilize advanced gait joint trajectories in which hip joint component velocities are non-zero for the hip joint components during transitions from swing states to stance states of the gait cycle.

12. The non-transitory computer readable medium of claim 10, wherein for advanced gait control the control system executes the program code to control the knee joint components to utilize advanced gait joint trajectories in which knee joint component velocities are non-zero for the knee joint components during transitions from stance states to swing states of the gait cycle.

13. The non-transitory computer readable medium of claim 11, wherein when an advanced gait trajectory is utilized during hip joint component swing, the control system executes the program code to employ an advanced gait trajectory in a subsequent hip joint component stance.

14. The non-transitory computer readable medium of claim 12, wherein when an advanced gait trajectory is utilized during knee joint component stance, the control system executes the program code to employ an advanced gait trajectory in a subsequent knee joint component swing.

15. The non-transitory computer readable medium of claim 10, wherein for advanced gait control the control system executes the program code to control the knee and hip joint components such that each step of the gait cycle occurs in substantially immediate succession following a previous step by way of hip joint component swing-to-stance extension, and/or knee joint component stance-to-swing flexion.

16. The non-transitory computer readable medium of claim 10, wherein the angular position is measured of a left stance/trailing leg during a single support dynamic state of the gait cycle to determine whether to take a step with the right leg, and the angular position is measured of a right stance/trailing leg during a single support dynamic state of the gait cycle to determine whether to take a step with the left leg.

17. The non-transitory computer readable medium of claim 10, wherein when it is determined that the advanced gait threshold condition is not satisfied, the control system executes the program code to employ standard gait control in which double support states are maintained between single support dynamic states, and a decision whether to step is made by sensing an angular position of the forward leg during the double support state.

18. A mobility device comprising:

an electronic control system for controlling operation of the at least one drive component to selectively configure and modulate the at least one joint component;

a plurality of sensors to detect a state of the at least one drive component and/or the at least one joint component; and the non-transitory computer readable medium according to claim 14, wherein the electronic control system executes the program code stored on the non-transitory computer readable medium.

19. The mobility device of claim 18, wherein the mobility device is a legged mobility exoskeleton device comprising a plurality of drive components that drive a plurality of joint components including at least knee joint components and hip joint components.

20. A control method of controlling a mobility device having a plurality of mobility device components including a right hip joint component and a right knee joint component corresponding to a right leg, and a left hip joint component and a left knee joint component corresponding to a left leg, the control method comprising the steps of:

providing said mobility device, said mobility device further including a control system for controlling operation of the mobility device components to selectively control the hip and knee joint components to perform a gait cycle;

providing within said mobility device a control application to be executed by the control system to control the gait cycle;

providing within said mobility device a plurality of sensors to detect a state of the hip and knee joint components to determine an angular position of the right leg and left leg during the gait cycle;

wherein the control system is configured to control the hip joint components and the knee joint components in either of a standard gait control or an advanced gait control;

the standard gait control comprising maintaining double support states in which both legs are in stance between single support dynamic states corresponding to a stepping state in which one leg is swinging while the opposing leg is a stance leg during stepping, and a decision whether to step is made by sensing an angular position of a forward leg during the double support states;

the advanced gait control comprising making a determination to initiate stepping during the single support dynamic state, thereby initiating a stepping motion in which steps are taken in immediate succession thereby minimizing a duration of double support states; and executing the control application with the control system further to perform the steps of:

controlling the hip joint and knee joint components to operate corresponding to the standard gait control;

sensing at least one of an angular position or an angular velocity of the stance leg during stepping during the single support dynamic state of the gait cycle;

determining whether the angular position or angular velocity surpasses an advanced gait threshold; and when it is determined that the angular position or angular velocity surpasses the advanced gait threshold, the control system switches control from the standard gait control to the advanced gait control, and when it is determined that the angular position or angular velocity does not surpass the advanced gait threshold the control system maintains control in the standard gait control.

* * * * *